United States Patent
Hildebrand et al.

(10) Patent No.: US 8,586,831 B2
(45) Date of Patent: Nov. 19, 2013

(54) EARLY FLOWERING MUTANT CHIA AND USES THEREOF

(75) Inventors: David Hildebrand, Lexington, KY (US); Watchareewan Jamboonsri, Bangkok (TH); Timothy Phillips, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 551 days.

(21) Appl. No.: 12/609,946

(22) Filed: Oct. 30, 2009

(65) Prior Publication Data

US 2013/0007909 A1    Jan. 3, 2013

Related U.S. Application Data

(60) Provisional application No. 61/197,952, filed on Oct. 31, 2008.

(51) Int. Cl.
*A01H 5/00* (2006.01)
*A01H 5/10* (2006.01)

(52) U.S. Cl.
USPC .......................................... 800/295; 435/410

(58) Field of Classification Search
None
See application file for complete search history.

(56) References Cited

PUBLICATIONS

Cahill et al 2002, The Journal of Heredity 93(1): 52-55.*
Chen et al, Derwent Abstract 2008-J29315 of Chinese Patent Publication CN 101120654 A, published Feb. 13, 2008.*
Coates et al 1996, Industrial Crops and Products 5: 229-233.*

* cited by examiner

*Primary Examiner* — David H Kruse
(74) *Attorney, Agent, or Firm* — McDermott Will & Emery LLP

(57) ABSTRACT

The invention relates to early flowering Chia (*Salvia hispanica* L.) strains that are suitable for culturing in a temperate area for seed production. Mutations are introduced to wild type chia seeds. Desired mutant progeny having normal appearance and an altered flora organ development is subsequently identified.

18 Claims, 3 Drawing Sheets

EARLY FLOWERING MUTANT CHIA AND USES THEREOF

CROSS REFERENCE TO RELATED APPLICATIONS

This application claims the benefit of U.S. Provisional Application Ser. No. 61/197,952, filed Oct. 31, 2008, which is incorporated by reference in its entirety.

GOVERNMENT SUPPORT

The work described herein was funded, in whole or in part, by Grant Number 2008-34419-19015 from the United States Department of Agriculture. The United States government may have certain rights in the invention.

FIELD OF THE INVENTION

The invention relates to early flowering chia (*Salvia hispanica* L.) strains that are suitable for culturing in a temperate area for seed production.

BACKGROUND OF THE INVENTION

Chia (*Salvia hispanica* L.) is a member of the Labiateae or Lamiaceae or mint family. This annual seed crop has a chromosome number of 2n=12. Chia and chia oil are used as human food, animal feed, drying oil in paints, ingredient in cosmetics. Chia seed is a good source of natural lipid antioxidants. Flavonol glycosides, chlorogenic acid, caffeic acid and myricetin are found in chia extracts. The antioxidant activity of a fiber-rich fraction of chia flour was found to be higher than many cereals and similar to drinks such wine, tea, coffee and orange juice. Chia seed coats are high in fiber which becomes mucilagenous and expands considerably when soaked in water. The fiber contains xylose, glucose and glucuronic acid monomers. One report finds that a fiber-rich fraction of chia flour has 56.5 g/100 g total dietary fiber content. The fiber-rich fraction water-holding capacity is 15.4 g/g. Chia seeds are about 20% protein. Chia is very high in omega-3 fatty acids. Diets supplemented with chia have been found to decrease risks from some type of cardiovascular diseases, cancers and diabetes. It has been reported that inclusion of chia in diets decreases tumor weight and metastasis number and also inhibits growth and metastasis in a murine mammary gland adenocarcinoma. Long-term dietary supplementation with chia attenuated a major cardiovascular risk factor and emerging factors safely beyond conventional therapy, while maintaining good glycemic and lipid control in people with well-controlled type-2 diabetes. Omega-3 fatty acids are reported to have a significant benefit in psychiatric disorders such as prevention and/or treatment of unipolar and bipolar depression.

Currently, chia is commercially grown in tropical and subtropical areas, e.g., areas in Argentina, Bolivia, Colombia, Mexico and Peru where latitude are ranged from 20°55'N to 25°05'S. However, in higher latitudes like Choele-Choele, (39°11'S) Argentina and Tucson (32°14'N), Ariz., USA, chia plants do not produce seeds since the seeds are killed by frost before they mature.

Efforts for improving chia seed production has largely been focused on selecting or breeding domesticated varieties of chia strains. However, lack of reliable sources of chia limits the potential to bring chia to the market as a new commercial crop. Therefore, there is a need to generate new chia strains that would allow chia seeds to be produced in much of the United States and other temperate regions.

SUMMARY OF THE INVENTION

The invention relates to early flowering Chia (*Salvia hispanica* L.) strains that are suitable for culturing in a temperate area for seed production. Mutations are introduced to wild type chia seeds. Desired mutant progeny having normal appearance and an altered flora organ development is subsequently identified.

In one aspect, the invention provides a mutant *Salvia hispanica* L. plant exhibiting early flowering phenotype as compared to a wild type *Salvia hispanica* L. plant having the same genetic background.

In certain embodiments, the mutant *Salvia hispanica* L. plant has a truncated vegetative growth period, as compared to that of a wild type *Salvia hispanica* L. plant having the same genetic background, when grown under a photoperiod of at least 12 hours per day.

In certain embodiments, the mutant *Salvia hispanica* L. plant develops floral organ when grown in a temperate area under a photoperiod of at least 12 hours per day, at least 13 hours per day, at least 14 hours per day, or at least 15 hours per day.

In certain embodiments, the early flowering phenotype of the mutant *Salvia hispanica* L. strain is obtained by chemical-induced mutagenesis. In certain embodiments, the early flowering phenotype of the mutant *Salvia hispanica* L. strain is obtained by radiation-induced mutagenesis.

In another aspect, the invention provides a mutant *Salvia hispanica* L. seed having a heritable trait that confers early flowering phenotype.

In certain embodiments, the mutant *Salvia hispanica* seed is selected from a strain listed in Table 3. In an exemplary embodiment, the mutant *Salvia hispanica* L. seed is designated as *Salvia hispanica* L. line G8, under ATCC Patent Deposit Designation No. PTA-10460.

The invention also provides a mutant *Salvia hispanica* L. plant, or a part thereof, produced by growing a mutant *Salvia hispanica* L. seed of the invention.

Pollen, ovules, seeds and tissue cultures of regenerable cells from the mutant *Salvia hispanica* L. plants of the invention are also provided.

In another aspect, the invention provides a method for producing a mutant *Salvia hispanica* L. strain having an altered flora organ development, as compared to a wild type *Salvia hispanica* L. having the same genetic background, comprising: (1) introducing one or more mutations to a population of *Salvia hispanica* seeds; (2) planting and growing the *Salvia hispanica* seeds of step (1); and (3) selecting emergent *Salvia hispanica* L. plants, or progeny thereof, that are normal in appearance and have an altered flora organ development.

In certain embodiments, the altered flora organ development is early flowering.

In certain embodiments, the mutations are induced by a chemical mutagen. In certain embodiments, the chemical mutagen is Ethylmethane Sulphonate (EMS). In an exemplary embodiment, *Salvia hispanica* L. seeds are treated with 6% (v/v) EMS.

In certain embodiments, the mutations are induced by radiation. In certain embodiments, the radiation is γ-ray. In an exemplary embodiments, *Salvia hispanica* L. seeds are treated with γ-ray at 500 gray.

In another aspect, the invention provides a method for increasing the production of *Salvia hispanica* L. seeds, wherein said *Salvia hispanica* L. is grown in a temperate area, comprising: (1) introducing one or more mutations to a population of *Salvia hispanica* L. seeds; (2) planting and growing the *Salvia hispanica* L. seeds of step (1); (3) selecting emergent *Salvia hispanica* L. plants, or progeny thereof, that are normal in appearance and have early flowering phenotype; and (4) harvesting and growing the seeds from the early flowering *Salvia hispanica* L. strains selected in step (3).

In certain embodiments, the *Salvia hispanica* L. is grown in a temperate area under a photoperiod of at least 12 hours per day, at least 13 hours per day, at least 14 hours per day, or at least 15 hours per day.

DETAILED DESCRIPTION OF THE INVENTION

1. Overview

Figure 1:
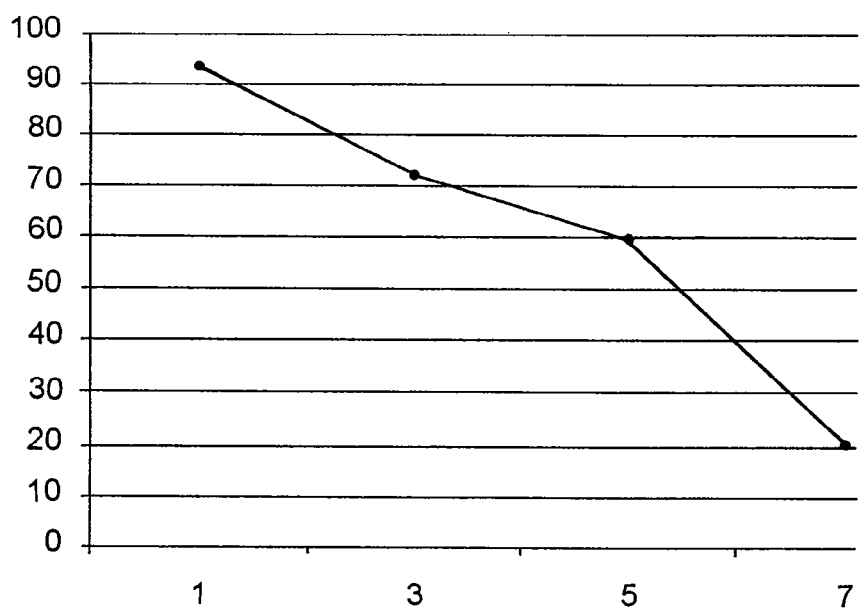
FIG. 1 is a graph showing the germination rate of chia seeds treated with different concentrations of EMS.

Chia (*Salvia hispanica* L.) is a short day plant that flowers only when the night is longer than a critical length (e.g., 12 hours). Wild type chia plants do not flower under the long days of summer. In addition, wild type chia plants do not flower if a pulse of artificial light is shone on the plant for several minutes during the middle of the night, as it requires a consolidated period of darkness before floral development can begin. As a result, in temperate areas, wild type chia plants typically flower in fall and are unable to set seeds before killing frost. Currently, chia is commercially grown in Argentina, Mexico and Bolivia.

In one aspect, the invention provides mutant chia strains that require shorter period of darkness for floral development, as compared to wild type chia having the same genetic background, and are able to flower during longer days of summer. Early flowering chia strains of the invention are particularly useful for culturing in temperate areas as the early flowering strains have sufficient time for seeds to mature before killing frost.

In another aspect, the invention provides a method for producing a mutant chia strain having an altered flora organ development (e.g., early flowering) as compared to a wild type chia having the same genetic background, by (1) introducing one or more mutations to a population of chia seeds, (2) growing the mutagenized seeds, and (3) selecting chia plants (or progeny thereof) that are normal in appearance and have an altered flora organ development (e.g., early flowering).

The chia seeds of the invention provide a natural source of omega-3 fatty acids, antioxidants and dietary fiber. They can be used as a new food source and offer a great opportunity to improve human nutrition.

2. Methods for Generating Mutant Chia Strains

In one aspect, the invention provides a method for producing a mutant chia strain having an altered flora organ development (e.g., early flowering) as compared to a wild type chia strain having the same genetic background, by (1) introducing one or more mutations to a population of chia seeds, (2) growing the mutagenized seeds, and (3) selecting chia plants (or progeny thereof) that are normal in appearance and have an altered flora organ development (e.g., early flowering).

Within the invention, the term "wild type" chia strain refers to a "normal" chia strain occurring in nature without any known mutation. Wild type chia strains include both uncultivated/non-domesticated chia strains, as well as cultivated/domesticated chia strains (including domesticated chia strains obtained from breeding). In certain embodiments, a wild type chia strain is considered as having the same genetic background as a mutant chia strain of the invention if the wild type chia strain serves as a starting material for producing the mutant chia strain. Characteristics of certain exemplary wild type chia strains are summarized below in Table 1.

TABLE 1

Agricultural and phenological characteristic of four lines of *Salvia hispanica* L. grown in Temalacacingo, Mexico

| Ecotype | Cycle (days) | Height (cm) | Branches (no.) | Heads (no.) | Yield (g/plant) | Seed weight (g/1,000 seeds) |
|---|---|---|---|---|---|---|
| Temalacacingo | 102 | 99.8 | 9.5 | 16.6 | 4 | 1.1 |
| Tlalapa | 112 | 103.3 | 9 | 14.8 | 2.4 | 0.8 |
| Chia poblana | 115 | 102.8 | 10.4 | 17.1 | 3.1 | 1.2 |
| Chia pinta | 98 | 91.2 | 9.2 | 15.3 | 3.9 | 1.2 |

Source: Hernandez Gomez, J.A. 1994, Chia (*Salvia hispanica*): antecedentesy prespectivas en Mexico, in Premier simposium international sobre etnobotanica en Mesoamerica, ed. J.A. Cuevas Sanches, E. Estrada Lugo, and E. Cedillo Portugal, 173-80 Chapingo, Mexico: Universidad Autonoma Chapingo., in ed. R. Ayerza and W. Coates, 2005, Chia: Rediscovering a forgotten crop of the Aztecs, The University of Arizona Press, Tucson, Arizona, 197 pp.

Any known mutagenesis technique can be used to obtain mutant chia strains of the invention, including, but not being limited to, chemical treatment, irradiation, or by DNA insertion of T-DNA or transposons from the host or from a heterologous origin, using techniques well known to the skilled artisan in this field.

For example, mutations can be introduced by chemical treatment with a mutagen such as ethyl methanesulfonate (EMS), methyl methanesulfonate (MMS), methyl-N-nitrosourea (MNU), bleomycin, and the like. In an exemplary embodiment, wild type chia seeds are treated with EMS. The mutagenized seeds are then planted in soil, and early flowering chia strains are selected from the emergent plants, or progeny thereof. In an exemplary embodiment, wild type chia seeds are treated with 6% (v/v) EMS.

Mutation can also be introduced by irradiation, for example, by UV light, X-rays, γ-rays, alpha particles, or fast neutrons. In an exemplary embodiment, wild type chia seeds are treated with γ-rays. The mutagenized seeds are then planted in soil, and early flowering chia strains are selected from the emergent plants, or progeny thereof. In an exemplary embodiment, wild type chia seeds are treated with γ-ray at 500 gray.

Mutation can also be introduced by a mobile DNA sequence (a T-DNA) or by a transposon. T-DNA mutagenesis may be carried out by known methods, e.g., via Agrobacterium (Hoekema et al., A Binary Plant Vector Strategy Based on Separation of Vir- and T-Region of the Agrobacterium tumefaciens Ti-Plasmid, Nature, 303: 179-180, 1983; U.S. Pat. No. 5,149,645). Transposon refers to a natural DNA sequence able to move or "jump" to different locations in the genome. Through insertion into a gene and resulting gene disruption, the transposon causes a mutation in the gene. Transposons have been found in bacteria, Drosophila, yeast, nematodes, plants and mammals. Transposon insertion mutagenesis may be done by well-known methods (Fedoroff et al., Cloning of the Bronze Locus in Maize by A Simple and Generalizable Procedure Using the Transposable Controlling Element Activator (Ac), Proc. Natl. Acad. Sci. USA, 81(12): 3825-3829, 1984; U.S. Pat. Nos. 4,732,856 and 5,013,658). The transposon may be an autonomous transposon, a non-autonomous transposon, or an autonomous/non-autonomous transposon system.

The mutant chia strains of the invention can be generated by random mutagenesis, for example, by treating a population of chia seeds with a chemical mutagen or radiation, or by randomly insertion of a mobile DNA sequence (e.g., transposon) into the genome. Desirable mutant strains can be subsequently screened, either by selection of a particular phenotype (e.g., early flowering), or by genetic analysis (e.g., PCR) to identify a strain that carries the mobile DNA sequence being inserted.

The mutant chia strains of the invention can also be generated by introducing mutations to genes that regulate floral organ development. In plants, daylength is perceived by leaves through the influence of red, far red and blue light on phytochromes, which induces a mobile signal, known as florigen, to move through the phloem to apical meristems. In the apical meristems, florigen causes changes in the expression of genes which alters the developmental program of the meristems to produce flowers instead of leaves. Numerous genes have been reported to influence floral induction in *Arabidopsis* and rice. See, e.g., Fornara, et al., 2009, *Arabidopsis* DOF Transcription Factors Act Redundantly to Reduce CONSTANS Expression and Are Essential for a Photoperiodic Flowering Response, Developmental Cell 17:75-86; Ishikawa et al., 2009, Phytochrome dependent quantitative control of Hd3a transcription is the basis of the night break effect in rice flowering, Genes & Genetic Systems 84:179-184; Komiya et al., 2009, A gene network for long-day flowering activates RFT1 encoding a mobile flowering signal in rice, Development 136:3443-3450; Notaguchi et al., 2008, Long-Distance, Graft-Transmissible Action of *Arabidopsis* FLOWERING LOCUS T Protein to Promote Flowering, Plant and Cell Physiology 49:1645-1658; Ryu et al., 2009, OsMADS50 and OsMADS56 function antagonistically in regulating long day (LD)-dependent flowering in rice, Plant Cell and Environment 32:1412-1427; Stangeland et al., 2009, AtMBD8 is involved in control of flowering time in the C24 ecotype of *Arabidopsis thaliana*, Physiologia Plantarum 136:110-126; Strasser et al., 2009, A complementary role for ELF3 and TFL1 in the regulation of flowering time by ambient temperature, Plant Journal 58:629-640; Yoshida et al., 2009, Possible role of EARLY FLOWERING 3 (ELF3) in clock-dependent floral regulation by SHORT VEGETATIVE PHASE (SVP) in *Arabidopsis thaliana*, New Phytologist 182:838-850. Hou and Yang (Functional Analysis of FT and TFL1 Orthologs from Orchid (Oncidium Gower Ramsey) that Regulate the Vegetative to Reproductive Transition, Plant and Cell Physiology 50:1544-1557, 2009) describe two genes in orchids that regulate flowering. Chia genes of similar functions can be identified (e.g., by sequence homology) as potential mutation targets.

In another aspect, the invention provides a method for increasing the production of chia seeds from chia plants that are cultured in a temperate area, comprising: (1) introducing one or more mutations to a population of chia seeds; (2) growing the mutagenized seeds, (3) selecting chia plants (or progeny thereof) that are normal in appearance and have an early flowering phenotype, and (4) harvesting and growing the seeds from the early flowering chia strains selected in step (3). In certain embodiments, the chia plants that are cultured in a temperate area under a photoperiod of at least 12 hours per day, at least 13 hours a day, at least 14 hours a day, or at least 15 hours a day.

3. Mutant Chia Strains

In another aspect, the invention provides mutant chia strains exhibiting early flowering phenotype as compared to a wild type chia having the same genetic background.

There are no known wild type chia strains that can set seed and mature in growing seasons as short as those in most temperate areas (including most growing regions in the U.S.). The inventors have tested several wild type chia strains from various local and internet sources, including a number of promising lines from Joseph Cahill (Cahill, J. 2003, Ethnobotany of Chia, *Salvia hispanica* L. (Lamiaceae), Economic Botany 57 (4): 604-618; Cahill, J. 2004, Genetic diversity among varieties of Chia (*Salvia hispanica* L.), Genetic Resources and Crop Evolution 51:773-781) and additional lines purchased in local Hispanic markets. Seven of these have been evaluated in the field in Lexington, Ky. and none of them have been able to set seed in local growing conditions. Some began flowering in October but were killed by frost before seed maturation. In addition, the inventors have consulted extensively with Joseph Cahill who has evaluated various chia strains from around the world. None of the strains the inventors or Joseph Cahill evaluated can be induced to flower or set seed until the daylength reaches about below 12 hours per day.

In contract, the early flowering chia strains of the invention allow chia seeds to be produced and mature in much of the United States and other temperate areas. In certain embodiments, the mutant chia strains of the invention have a truncated vegetative growth period, as compared to that of a wild type chia having the same genetic background, when grown under a photoperiod of at least 12 hours per day. In certain embodiments, the mutant chia strains of the invention develop floral organ when grown in a temperate area under a photoperiod of at least 12 hours per day, at least 13 hours a day, at least 14 hours a day, or at least 15 hours a day.

A temperate area typically refers to an area within the north temperate zone (extending from the Tropic of Cancer, at about 23.5 degrees north latitude, to the Arctic Circle, at approximately 66.5 degrees north latitude), or the south temperate zone (extending from the Tropic of Capricorn, at approximately 23.5 degrees south latitude, to the Antarctic Circle, at approximately 66.5 degrees south latitude).

In an exemplary embodiment, certain mutant chia plants of the invention showed floral induction 55 days after planting, while wild type chia of the same genetic background are unable to produce any flower buds when grown under the same condition.

In an exemplary embodiment, certain mutant chia plants of the invention showed floral development under a photoperiod of at least 14 hours per day, or at least 15 hours per day. Wild type chia having the same genetic background are unable to produce any flower buds when grown under the same condition (see e.g., Table 2).

In an exemplary embodiment, certain mutant chia plants of the invention showed floral development under a photoperiod of at least 12 hours per day, or at least 13 hours per day. Wild type chia having the same genetic background are either unable to produce any flower buds, or require longer vegetative growth period when grown under the same condition (see e.g., Table 2).

Additional exemplary mutant chia strains of the invention are listed in Table 3.

In another aspect, the invention provides mutant chia seeds having a heritable trait that confers early flowering phenotype. Seeds from one exemplary early flowering chia strain, designated as *Salvia hispanica* L. line G8, were deposited on Oct. 30, 2009 with American Type Culture Collection (ATCC), P.O. Box 1549, Manassas, Va. 20108, USA, under ATCC Patent Deposit Designation No. PTA-10460.

The invention also provides mutant chia plants, or a part thereof, produced by growing the chia seeds of the invention.

Pollen, ovules, seeds and tissue cultures of regenerable cells from the mutant chia plants of the invention are also provided.

4. Uses of Mutant Chia Strains

The chia seeds of the invention provide a natural source of omega-3 fatty acids, antioxidants and dietary fiber. They can be used as a new food source and offer a great opportunity to improve human nutrition.

Until the late 1990's, chia seeds were only consumed by small, isolated groups of people in Mexico, Guatemala, Nicaragua as well as the southern U.S. (California and Arizona) Primarily the seeds were mixed in water, along with lime juice and sugar, and consumed as a refreshing beverage. The early flowering chia strains of the invention promote production of chia seeds in temperate areas.

Chia seeds are known to contain high level of α-linolenic acid ("ALA"), an omega-3 fatty acid, and linoleic acid ("LA"), an omega-6 fatty acid, in a unique ratio of approximately 3.3:1. The seed provides approximately 33% seed oil, 21% protein, 41% total dietary fiber and high levels of minerals such as calcium, iron, magnesium and phosphorus. Therefore, chia seeds are an excellent source of essential polyunsaturated fatty acids, protein, fiber and minerals. The composition of chia seeds is known to those skilled in the art. Many unique properties of chia seeds are disclosed in U.S. Patent Publication Nos. 2002/0155182, 2004/0185129, 2008/0305190 and U.S. Pat. No. 6,827,965, the disclosures which are hereby incorporated by reference in their entirety.

In particular, chia seeds contain an oil rate varying between 27-33% and offers one of the highest percentage of α-linolenic acid (about 60-70%) known in nature. α-linolenic acid is known to reduce the risk of cardiovascular disease.

In addition to health foods, traditional industrial uses of ω3 oils include, e.g., wood coatings, flooring manufacturing (e.g. linoleum), or printing inks.

Chia seeds also contain about 19%-23% of proteins. This percentage is favorably compared to other nutritional grains such as wheat (14%), corn (11%), rice (8.5%), oats (15.3%), barley (9.2%) and amaranth (6.7%). In addition, unlike the above compared grains, chia seeds contain all 9 essential amino acids in an optimal proportion.

Water and methanol extracts pertaining to degreased chia seeds have demonstrated a strong antioxidizing activity. Most important isolated antioxidants of chia seeds are Vitamin E, chlorogenic acid, caffeic acid and flavonol glycosides.

Chia may also be the best source of healthful soluble fiber known. Chia seed possesses 5% of soluble fiber which appears as mucilage when the seed is humidified.

Adding whole chia seed to animal diets greatly increases the nutritional value of the resulting eggs and poultry meat.

It has also been reported that chia can greatly enhance endurance and muscle strength.

Recently, there has been considerable recent interest in flax (*Linum usitatissimum*) as a high ω3 fatty acid and high fiber food additive and supplement. There is also considerable potential as feed in fish farming and production of high ω3 eggs, a market that continues to expand. Chia is much higher both in ω3 fatty acid levels (>10% more) and healthful soluble fiber than flax and therefore has greater potential in new healthful foods and feeds. In addition, chia seeds, unlike flax seeds, contain no gluten, cyanogenic glycosides, phytoestrogenic lignans, or vitamin B antagonists.

The inventors have evaluated both flax and chia as new crops for Kentucky farmers at the University of Kentucky north farm in Lexington for four growing seasons, and acquired and evaluated the most promising germplasm for these two species for several additional years. Flax has shown little potential for high yields in Kentucky. Chia on the other hand, has shown considerable yield potential, vigorous growth with minimum inputs, and watering only at low levels under severe drought (and this insufficient to stimulate weed growth). However, no known wild type chia strains are able to set and mature seeds when grown in Kentucky area. The early flowering mutant chia strains of the invention allow chia seeds to be produced in a temperate region and help bring chia to the market as a new commercial crop.

Chia seeds are a critical component of the well known "Chia Pet" due to the seeds' ability to readily absorb and retain moisture, its high level of germination and its sticky muco-polysaccharide outer seed coating.

Some commercial operators hydrate and separate seed coat polysaccharide from water pre-soaked seeds to derive a separated seed gel coat useful in the preparation of gel enhanced beverages and later apply the whole seed for the treatment and prevention of human diseases. The operators also produce expeller pressed flour from chia seeds, which are used either alone or admixed with other grain or legume seed flours, meat based seasonings, vegetable based pastes, diary-based products and the like.

Other details concerning the use of chia are found in the Opinion of Scientific Panel on Dietetic Products, Nutrition and Allergies on a request from the Commission related to the safety of chia (*Salvia hispanica* L.) seed and ground whole chia seed as a novel food ingredient intended for use in bread, e.g., the EFSA Journal 278, 1-2; (2005); entitled "Opinion of the Scientific Panel on Dietetic Products, Nutrition and Allergies on a request from the Commission related to the safety of chia (*Salvia hispanica* L.) seed and ground whole chia seed as a novel food ingredient intended for use in bread," the disclosure which is hereby incorporated by reference in its entirety.

Finally, the mutant chia strains of the invention can be used to study the genetic control of flowering in chia and the genetic basis of the early flowering phenotype. Useful techniques include, e.g., examining the inheritance of early flowering traits backcrossed with the parental genotype, or allelism studies among the different early flowering chia strains.

EXEMPLIFICATION

The invention now being generally described, it will be more readily understood by reference to the following examples, which are included merely for purposes of illustration of certain aspects and embodiments of the present invention, and are not intended to limit the invention.

Example 1

Materials and Methods

Seed Materials

Chia seeds used in this experiment were obtained from www.chiaseedandoil.com shipped from Tucson, Ariz. In certain experiments, seeds of the cultivar "Pinta" were used.

Mutagenesis

EMS mutagenesis: Seeds were soaked in ethyl methanesulfonate (EMS) diluted with deionized water at different concentrations for 6 hours at room temperature. Seeds were rinsed in excess amounts of water four times. Seeds were then pipetted on the surface of potting mix. Seed germination was observed at 7, 14 and 21 days after planting.

Gamma ray mutagenesis: Seeds were irradiated in a Shepherd Mark I—30 Irradiator at the Department of Radiation Medicine, University of Kentucky.

Screening for Early Flowering Mutants in the $M_2$ Population

In order to screen for early flowering mutants, $M_2$ seeds were planted in bulk in the field of Spindletop farm in Lexington, Ky. in summer 2008, (longitude W84.5, latitude N38.1). The planting date was July $25^{th}$ where the day length was 14 hours and 18 minutes. Approximately 1,000 seeds were planted in 4 rows of 5×20 ft plots. There were 209 plots of $M_2$ EMS-mutagenized plants, 232 plots of $M_2$ gamma-mutagenized plants and 11 plots of non-mutagenized plants. Border rows were non-mutagenized plants. No applications of herbicides, pesticides or fertilizer were made. The plots were irrigated just enough for minimal plant growth due to the severe drought in 2008.

Day lengths were obtained from the U.S. Naval Observatory Astronomical Applications Department, entitled "Complete Sun and Moon Data for One Day."

Critical Day Length

A study on critical daylength of the early flowering mutants was performed in a greenhouse. Chia seeds were planted on Feb. 19, 2009. $M_3$ seedlings were grown under a photoperiod of 14.5 hours until having at least six nodes (1 month old). The seedlings were then induced to flower under four different light treatments. One treatment was exposed to daylight for 12 hours and covered in a dark tent for 12 hours. The other three treatments were treated the same except for having extended light beyond 12 hours of daylight for 1, 2 and 3 hours respectively.

Light tents were made of vinyl plastic sheet. It was white-coated on one side and black-coated on the other side. The sheet was cut and stapled into cubic shape of 1.2 m$^3$. The tents were supported by jointed plastic pipes. The extended light was given by using new 60-Watt clear incandescent bulbs. The light intensity was measured by using the F400-VisNIR fiber optic cable (design for a sensor) with the instrument (EPP2000 fiber optic spectrometer from StellarNet Inc.). The bar sensor was placed diagonally in a light tent and about 3 feet below light bulbs. A spot sensor was also used to measure light intensity on the corners of a light tent. The average intensity of the extended light was 13 µmoles (µEinsteins m$^{-2}$ s$^{-1}$) at the top of the plant canopies. Light intensity was 0.01 micromoles when the light was switched off. The greenhouse temperature was set for 29° C. high and 21° C. low. The actual highest temperature in the light tents was 31° C. and the lowest was 21° C.

One light treatment contained 16 experimental units. One experimental unit consisted of 6 plants from the same line. Each experimental unit was randomized for placement in a light treatment. Flowering of mutant plants was monitored and compared with wildtype.

Field Test of Early Flowering Mutants

Seeding was done by using a small push-planter in rows. The planting date was May 20, 2009 where the day length was 14 hours and 23 minutes. The rows were 20 feet in length and 3 feet apart. No application of herbicide, pesticide or fertilizer was done to the plot. Limited weeding was done before the canopy closed. Flowering and seed set were monitored throughout the growing season.

Example 2

Optimizing EMS-Induced Mutagenesis

Chemical mutagenesis by ethyl methanesulfonate (EMS) was used in an attempt to produce early flowering mutants. Various concentrations of EMS were evaluated from 0.1 to 8% at small increments including the standard 0.25% used for *Arabidopsis* and 6% EMS was found to produce ~50% seedling lethality and 0.02% white plants among the surviving 50% (Redei et al., 1992; Weigel et al., 2002). Lethality was ~80% with 8% EMS.

Thus the optimal dose of EMS was studied to achieve about 50 percent germination rate. Chia seeds were treated with different concentrations of EMS, 0%, 3%, 5% and 7% respectively. Germination rate was observed as shown in FIG. 1.

From the germination chart, 50% germination can be obtained by treating seeds with a 6% EMS concentration. This concentration was found to be very high for EMS treatment compared to recommended EMS concentrations for other crops. Fatty acid mutations in flax was achieved by treating flax seeds with 0.4% EMS (Rowland and Bhatty, 1990). 0.2% of EMS was used in mutagenesis in *Arabidopsis* (Jander et al, 2003). The optimal dose of 6% EMS was applied to treat chia seeds in the chemical mutagenesis experiment.

The $M_1$ population number was calculated to give a probability to find early flowering mutation. $M_1$ population must be greater than 5,000 plants to yield at least 1 mutation/gene. $M_1$ seeds were sown in the winter of 2008. Over 6,000 EMS-mutagenized $M_1$ seedlings and 5,000 gamma-mutagenized $M_1$ seedlings were grown at a 14 hour photoperiod. At the 4-node stage, all $M_1$ seedlings were transferred to a greenhouse under the natural winter photoperiod in Lexington, Ky. without additional light (<12 h). $M_1$ plants were induced to flower by natural short days. The first flower bud on M1 plants was noticed at the fourth week of flowering induction. Physical abnormalities such as chlorophyll deficiency, fused leaf, twisted stem, double flower, varigation and different flower colors were found in the $M_1$ population. $M_2$ seeds were harvested in spring of 2008.

Example 3

Screening for Early Flowering Mutants in $M_2$ Population

Figure 2:
FIG. 2 is a picture showing an early flowering mutant chia plant among M2 gamma ray-mutagenized population.

Flowering was monitored of the M2 plants in the field in 2009 twice a week. Flower buds of the earliest flowering mutants formed 55 days after planting where the day length was 12 hours and 16 minutes. No flower buds were found in control plots and in non-mutagenized border rows on that date. FIG. 2 shows an early flowering plant among $F_2$ population in the field. There were 22 early flowering plants found in approximately 165,000 plants of the $M_2$ EMS-mutagenized population which is 0.013%. In the gamma radiation-mutagenized population of approximately 185,000 plants, there were 46 early flowering plants which is 0.024%. The rest of the field started to form flower buds on the second week of October. Early flowering plants were marked and transferred to a greenhouse before the killing frost on the third week of October. Non-mutagenized plants were killed by frost before blooming (petal opening). FIG. 2 is a picture showing an early flowering mutant plant among $M_2$ gamma ray-mutagenized population.

Example 4

Critical Day Length Study in $M_3$ Mutants

A study was conducted to determine the day length required for flowering induction in early flowering mutants.

Six experimental units were EMS-mutants, seven units were gamma ray mutants, and three units were wild type. Flower buds were noticed on some mutant plants after seven days of light treatment. The experiment was carried on for five more weeks. Flowering in different experimental units in different day length is shown in Table 2. Flower buds on wild type plants were not noticed until the fifth week of 12-hour and 13-hour light treatments and not observed at 14-hour or 15-hour.

plants were induced to flower at a daylength ≤12 h were moved to longer daylengths flowering ceased and vegetative growth resumed.

Figure 3:
FIG. 3 is a picture showing flowering of early flowering chia plants in the field in Lexington, Ky., July 2009.

We saw remarkable uniformity in flowering of most $M_3$ plants of the $M_2$ families with little segregation for flowering phenotype as illustrated in FIG. 3.

Further, the early flowering trait was found to be stable over two generations and for two seasons in the field and in a controlled study in a greenhouse.

TABLE 2

Flowering of different M3 mutant lines under different photoperiods compared to wild type

| line | | | 12 hours | | | 13 hours | | | 14 hours | | | 15 hours | | |
|---|---|---|---|---|---|---|---|---|---|---|---|---|---|---|
| | | | 3 W | 4 W | 5 W | 3 W | 4 W | 5 W | 3 W | 4 W | 5 W | 3 W | 4 W | 5 W |
| A | WTF | D | | | ✽ | | | | | | | | | |
| B | WTR | D | | | ✽ | | | ✽ | | | | | | |
| C | WTR | W | | | ✽ | | | ✽ | | | | | | |
| D | EMS | D | ✽ | ✽ | ✽ | ✽ | ✽ | ✽ | ✽ | ✽ | ✽ | ✽ | ✽ | ✽ |
| E | EMS | D | ✽ | ✽ | ✽ | ✽ | ✽ | ✽ | ✽ | ✽ | ✽ | ✽ | ✽ | ✽ |
| F | EMS | D | | ✽ | ✽ | | ✽ | ✽ | | ✽ | | | | |
| G | EMS | D | ✽ | ✽ | ✽ | ✽ | ✽ | ✽ | | ✽ | ✽ | | ✽ | ✽ |
| H | EMS | W | ✽ | ✽ | ✽ | ✽ | ✽ | ✽ | | ✽ | ✽ | | ✽ | ✽ |
| I | EMS | W | ✽ | ✽ | ✽ | ✽ | ✽ | ✽ | ✽ | ✽ | ✽ | | | ✽ |
| J | γ | D | ✽ | ✽ | ✽ | ✽ | ✽ | ✽ | ✽ | ✽ | ✽ | ✽ | ✽ | ✽ |
| K | γ | D | ✽ | ✽ | ✽ | ✽ | ✽ | ✽ | ✽ | ✽ | ✽ | ✽ | ✽ | ✽ |
| L | γ | D | ✽ | ✽ | ✽ | ✽ | ✽ | ✽ | ✽ | ✽ | ✽ | ✽ | ✽ | ✽ |
| M | γ | D | ✽ | ✽ | ✽ | ✽ | ✽ | ✽ | ✽ | ✽ | ✽ | ✽ | ✽ | ✽ |
| N | γ | D | ✽ | ✽ | ✽ | ✽ | ✽ | ✽ | ✽ | ✽ | ✽ | ✽ | ✽ | ✽ |
| O | γ | D | ✽ | ✽ | ✽ | ✽ | ✽ | ✽ | ✽ | ✽ | ✽ | ✽ | ✽ | ✽ |
| P | γ | D | ✽ | ✽ | ✽ | ✽ | ✽ | ✽ | ✽ | ✽ | ✽ | ✽ | ✽ | ✽ |

WTF: wild type family;
WTR: wild type from random seeds;
EMS: EMS-mutagenized line;
γ: gamma ray-mutagenized line;
D: dark seed coat;
W: white seed coat;
3 W: at the third week of induction;
4 W: at the fourth week of induction;
5 W: at the fifth week of induction;
✽: flowering Example 5

Field Test of Early Flowering Mutants

Forty lines of $M_3$ early flowering chia mutants were planted in spring 2009 (May 20, 2009 where the day length was 14 hours and 23 minutes) at the Univ. KY Farm in Lexington, Ky. Twenty lines were EMS-mutagenized and the other twenty lines were gamma rat-mutagenized. Flower buds formed on some of the early flowering lines on Jul. 7, 2009, 47 days after planting when the daylength was 14 hours and 41 minutes.

In contrast, wild type chia strains, e.g., "chia pinta" (see Table 1) as well as mixed wild type chia strains were grown in the field in Lexington for multiple years, and none completed flowering and were long from producing seeds. "Chia pinta" strain flowers the earliest among known wild type strains (Table 3), but when grown outside tropical and subtropical regions (e.g., in Kentucky), chia pinta flowers much later than the mutant strains described in this invention.

Most of the new early flowering chia lines set seed and matured by early October, 2009. Some of the lines matured and produced harvest dry seeds as early as Sep. 16, 2009 when the daylength was 12 h and 23 min. We found in the wildtype plants the floral induction was reversible; when These new early flowering chia strains would allow chia to be produced in much of the United States and other temperate regions.

Example 6

Characterization of Exemplary Early Flowering Mutant Chia Strains

Table 3 summarizes maturation times and mean plant heights of some of the exemplary early flowering chia strains grown in the field in Lexington, Ky. in 2009. The planting date was May 20. The rows were planted ~92 cm apart and plants ~1 cm apart in the rows. No fertilizer, pesticides, irrigation or herbicides were applied. Weeds were mowed down between the rows in the middle of the growing season. Early flowering mutant chia strains were able to set seed and reach harvest maturity in the field in Lexington, Ky. in 2009 (Table 3). In contrast, none of the wild type parental strains (see Table 1) were even flowering when the new strains listed in Table 3 were already harvest mature.

TABLE 3

Maturation times and mean plant heights of exemplary early flowering mutant chia strains

| line | harvest maturity | days to maturity | plant height-cm |
|---|---|---|---|
| E2a | 8-Oct. | 141 | 157.5 |
| E2b | 8-Oct. | 141 | 0.0 |
| E5a | 13-Oct. | 146 | 132.1 |
| E5b | 8-Oct. | 141 | 0.0 |
| E6a | 8-Oct. | 141 | 180.3 |
| E8a | 28-Sep. | 131 | 137.2 |
| E8b | 8-Oct. | 141 | 154.9 |
| E9a | 8-Oct. | 141 | 149.9 |
| E9b | 8-Oct. | 141 | 142.2 |
| E10a | 8-Oct. | 141 | 132.1 |
| E10a | 8-Oct. | 141 | 149.9 |
| E11a | 8-Oct. | 141 | 157.5 |
| E11a | 8-Oct. | 141 | 157.5 |
| E12a | 8-Oct. | 141 | 152.4 |
| E12a | 6-Oct. | 139 | 132.1 |
| E15a | 5-Oct. | 138 | 137.2 |
| E15a | 5-Oct. | 138 | 157.5 |
| G1a | 5-Oct. | 138 | 129.5 |
| G1b | 5-Oct. | 138 | 132.1 |
| G2a | 8-Oct. | 141 | 139.7 |
| G2b | 8-Oct. | 141 | 149.9 |
| G3a | 16-Sep. | 119 | 144.8 |
| G3b | 16-Sep. | 119 | 157.5 |
| G4a | 6-Oct. | 139 | 139.7 |
| G4b | 8-Oct. | 141 | 157.5 |
| G5a | 8-Oct. | 141 | 185.4 |
| G5b | 8-Oct. | 141 | 193.0 |
| G6a | 8-Oct. | 141 | 160.0 |
| G6b | 8-Oct. | 141 | 165.1 |
| G7a | 28-Sep. | 131 | 152.4 |
| G7b | 8-Oct. | 141 | 162.6 |
| G8a | 16-Sep. | 119 | 129.5 |
| G8b | 16-Sep. | 119 | 127.0 |
| G9a | 8-Oct. | 141 | 119.4 |
| G9b | 5-Oct. | 138 | 129.5 |
| G10a | 16-Sep. | 119 | 137.2 |
| G10b | 16-Sep. | 119 | 152.4 |
| G11a | 8-Oct. | 141 | 149.9 |
| G11b | 5-Oct. | 138 | 160.0 |
| G12a | 8-Oct. | 141 | 152.4 |
| G12b | 6-Oct. | 139 | 165.1 |
| G13a | 8-Oct. | 141 | 147.3 |
| G13b | 8-Oct. | 141 | 144.8 |
| G14a | 8-Oct. | 141 | 149.9 |
| G14b | 8-Oct. | 141 | 144.8 |
| G15a | 5-Oct. | 138 | 149.9 |
| G15b | 5-Oct. | 138 | 154.9 |
| G16a | 8-Oct. | 141 | 129.5 |
| G16b | 5-Oct. | 138 | 139.7 |
| G17a | 8-Oct. | 141 | 124.5 |
| G17b | 8-Oct. | 141 | 137.2 |
| G18a | 8-Oct. | 141 | 152.4 |
| G18b | 8-Oct. | 141 | 175.3 |
| G19a | 8-Oct. | 141 | 142.2 |
| G19b | 8-Oct. | 141 | 142.2 |
| G20a | 8-Oct. | 141 | 149.9 |
| G20b | 8-Oct. | 141 | 139.7 |

Those skilled in the art will recognize, or be able to ascertain using no more than routine experimentation, many equivalents to the specific embodiments of the invention described herein. Such equivalents are intended to be encompassed by the following embodiments.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supercede any such material. The citation of any references herein is not an admission that such references are prior art to the present invention.

The invention claimed is:

1. A mutant *Salvia hispanica* L. plant that develops floral organ when grown in a temperate area under a photoperiod of at least 12 hours per day.

2. The mutant *Salvia hispanica* L. plant of claim 1, wherein the mutant plant develops floral organ when grown in a temperate area under a photoperiod of at least 13 hours per day.

3. The mutant *Salvia hispanica* L. plant of claim 1, wherein said mutant plant is obtained by chemical-induced mutagenesis.

4. The mutant *Salvia hispanica* L. plant of claim 1, wherein said mutant plant is obtained by radiation-induced mutagenesis.

5. A mutant *Salvia hispanica* L. seed having a heritable trait that confers early flowering phenotype, as represented by the development of floral organ in a *Salvia hispanica* L. plant when the plant is grown in a temperate area under a photoperiod of at least 12 hours per day.

6. The mutant *Salvia hispanica* seed of claim 5, wherein the seed is designated as *Salvia hispanica* L. line G8, representative seeds deposited under ATCC Patent Deposit Designation No. PTA-10460.

7. A mutant *Salvia hispanica* L. plant, or a part thereof, produced by growing the seed of claim 5.

8. Pollen of the mutant *Salvia hispanica* L. plant of claim 1 or 7.

9. An ovule of the mutant *Salvia hispanica* L. plant of claim 1 or 7.

10. A tissue culture of regenerable cells from the mutant *Salvia hispanica* L. plant of claim 1 or 7.

11. A *Salvia hispanica* L. seed from the mutant *Salvia hispanica* L. plant of claim 1 or 7, wherein said seed has a heritable trait that confers early flowering phenotype, as represented by the development of floral organ in a *Salvia hispanica* L. plant when the plant is grown in a temperate area under a photoperiod of at least 12 hours per day.

12. The mutant *Salvia hispanica* L. plant of claim 1, wherein the mutant plant develops floral organ when grown in a temperate area under a photoperiod of at least 14 hours per day.

13. The mutant *Salvia hispanica* L. plant of claim 1, wherein the mutant plant develops floral organ when grown in a temperate area under a photoperiod of at least 15 hours per day.

14. The mutant *Salvia hispanica* L. seed of claim 5, wherein said seed has a heritable trait that confers early flowering phenotype, as represented by the development of floral organ in a *Salvia hispanica* L. plant when the plant is grown in a temperate area under a photoperiod of at least 13 hours per day.

15. The mutant *Salvia hispanica* L. seed of claim 5, wherein said seed has a heritable trait that confers early flowering phenotype, as represented by the development of floral organ in a *Salvia hispanica* L. plant when the plant is grown in a temperate area under a photoperiod of at least 14 hours per day.

16. The mutant *Salvia hispanica* L. seed of claim 5, wherein said seed has a heritable trait that confers early flowering phenotype, as represented by the development of floral organ in a *Salvia hispanica* L. plant when the plant is grown in a temperate area under a photoperiod of at least 15 hours per day.

17. The mutant *Salvia hispanica* L. plant of claim 1 that produces mature seeds when grown in a temperate area under a photoperiod of at least 12 hours per day.

18. The mutant *Salvia hispanica* L. seed of claim 5 wherein the grown plant produces mature progeny seeds when grown in a temperate area under a photoperiod of at least 12 hours per day.

* * * * *